(12) United States Patent
Friedland

(10) Patent No.: US 10,881,815 B2
(45) Date of Patent: Jan. 5, 2021

(54) HERBAL DABBER VAPORIZER

(71) Applicant: David Friedland, Rialto, CA (US)

(72) Inventor: David Friedland, Rialto, CA (US)

( * ) Notice: Subject to any disclaimer, the term of this patent is extended or adjusted under 35 U.S.C. 154(b) by 155 days.

(21) Appl. No.: 16/148,087

(22) Filed: Oct. 1, 2018

(65) Prior Publication Data
US 2020/0101242 A1 Apr. 2, 2020

(51) Int. Cl.
*A61M 11/04* (2006.01)

(52) U.S. Cl.
CPC ... *A61M 11/042* (2014.02); *A61M 2205/3368* (2013.01)

(58) Field of Classification Search
CPC .................... A61M 11/042; A61M 2205/3368
USPC .......................................................... 392/386
See application file for complete search history.

(56) References Cited

U.S. PATENT DOCUMENTS

| | | | | | |
|---|---|---|---|---|---|
| 4,064,203 | A | * | 12/1977 | Cox .......................... | F24F 3/14 261/99 |
| 2003/0007887 | A1 | * | 1/2003 | Roumpos .................. | A61L 9/03 422/1 |
| 2006/0099540 | A1 | * | 5/2006 | Avelar ..................... | F21S 13/00 431/35 |
| 2009/0122516 | A1 | * | 5/2009 | Yang ........................ | A61L 9/122 362/96 |
| 2009/0123345 | A1 | * | 5/2009 | Yang ........................ | A61L 9/122 422/124 |
| 2015/0125136 | A1 | * | 5/2015 | Sanchez .................... | A61L 9/03 392/394 |
| 2016/0360788 | A1 | * | 12/2016 | Wang ..................... | A24F 47/008 |

* cited by examiner

*Primary Examiner* — Dana Ross
*Assistant Examiner* — Joseph W Iskra
(74) *Attorney, Agent, or Firm* — The Iwashko Law Firm, PLLC; Lev Ivan Gabriel Iwashko

(57) ABSTRACT

An herbal dabber vaporizer to heat materials therein to expel vapor therefrom, the herbal dabber vaporizer including a main body, including a main body base, a main body lid disposed above the main body based, at least one tube disposed between the main body base and the main body lid, at least one heating element connected to the at least one tube, and at least one stem to be inserted at least partially into a top aperture of the at least one tube to receive the materials therein, and a glass dome to cover the main body lid and the at least one stem, such that vapor generated from a heating of the materials causes the vapor to be generated within the glass dome, and then expelled out an aperture within the glass dome.

4 Claims, 6 Drawing Sheets

HERBAL DABBER VAPORIZER

BACKGROUND

1. Field

The present general inventive concept relates generally to a vaporizer, and particularly, to an improved herbal dabber vaporizer.

2. Description of the Related Art

Today's herbal vaporizer units usually function on a single heat source or single extraction chamber design, thereby, processing a limited amount of herbal material. Currently on the market, there are various herbal vaporizers, yet they tend to be limited in capacity and when overfilled, become unreliable resulting in uneven extraction or partial combustion.

Therefore, there is a need for an improved herbal vaporizer unit.

SUMMARY

The present general inventive concept provides an improved herbal dabber vaporizer.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing an herbal dabber vaporizer to heat materials therein to expel vapor therefrom, the herbal dabber vaporizer including a main body, including a main body base, a main body lid disposed above the main body based, at least one tube disposed between the main body base and the main body lid, at least one heating element connected to the at least one tube, and at least one stem to be inserted at least partially into a top aperture of the at least one tube to receive the materials therein, and a glass dome to cover the main body lid and the at least one stem, such that vapor generated from a heating of the materials causes the vapor to be generated within the glass dome, and then expelled out an aperture within the glass dome.

The aperture within the glass dome may be disposed at a top portion of the glass dome.

The herbal dabber vaporizer may further include a fan base, including a plurality of fan blades to spin and generate air that enters a bottom aperture of the at least one tube such that the vapor moves upward out of the at least one stem, and a fan motor to cause the fan blades to spin.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1A:
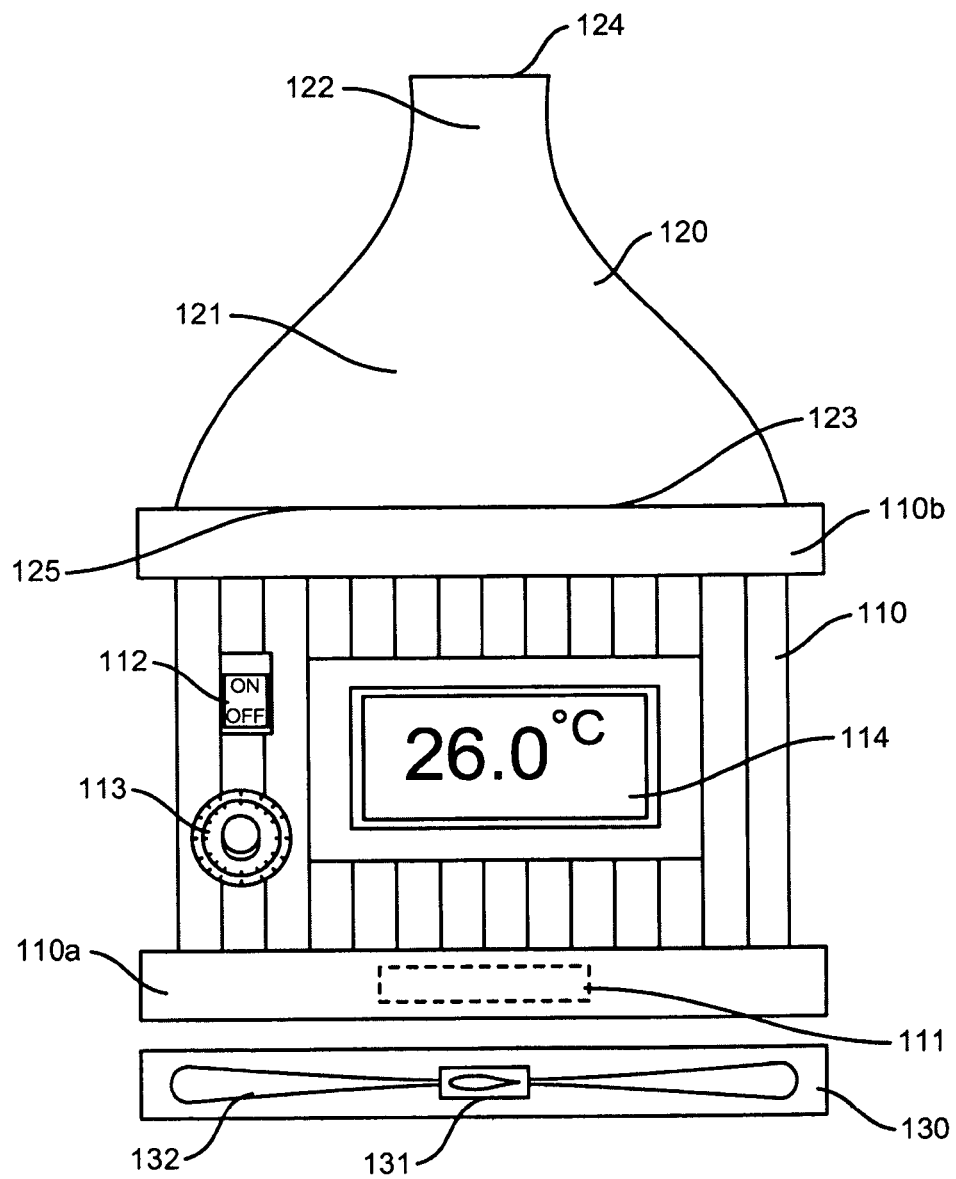
FIG. 1A illustrates a side perspective view of an herbal dabber vaporizer, according to an exemplary embodiment of the present general inventive concept.

FIG. 1A illustrates a side perspective view of an herbal dabber vaporizer 100, according to an exemplary embodiment of the present general inventive concept.

Figure 1B:
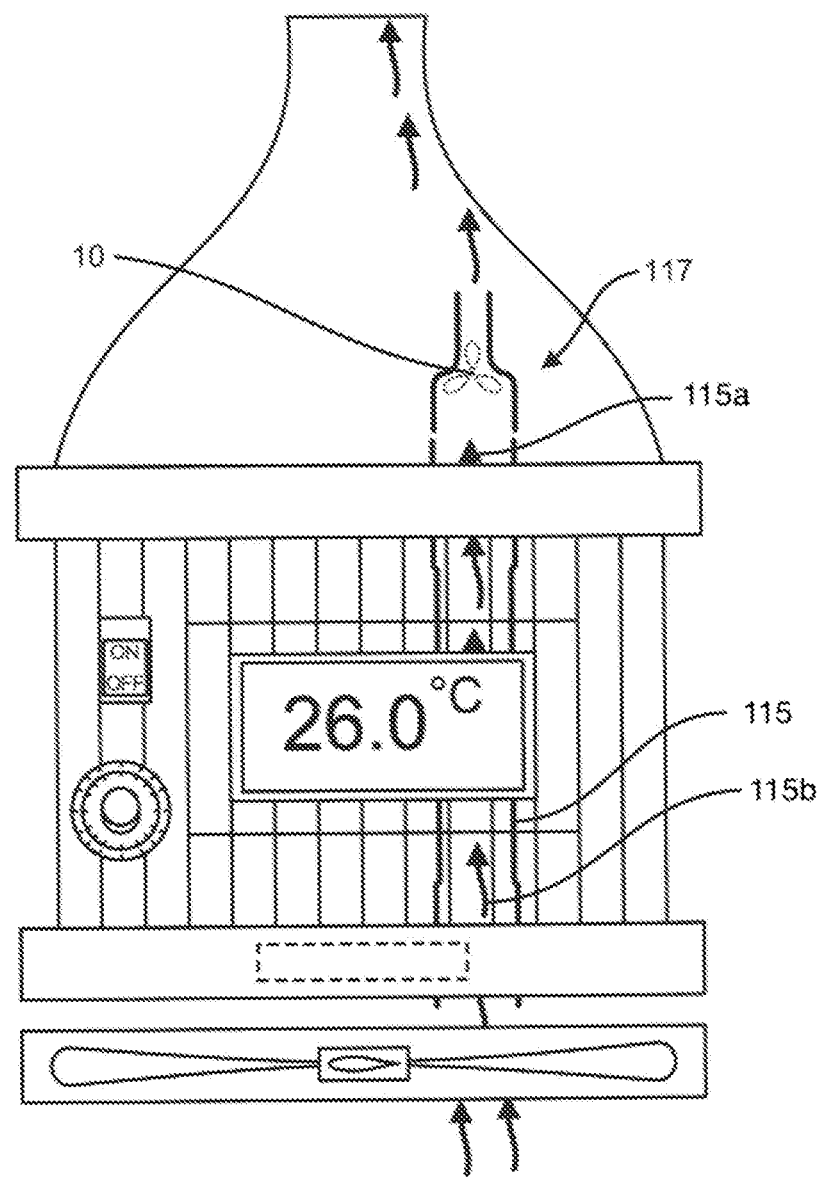
FIG. 1B illustrates another side perspective view of an herbal dabber vaporizer, according to an exemplary embodiment of the present general inventive concept.

FIG. 1B illustrates another side perspective view of the herbal dabber vaporizer 100, according to an exemplary embodiment of the present general inventive concept.

Figure 2:
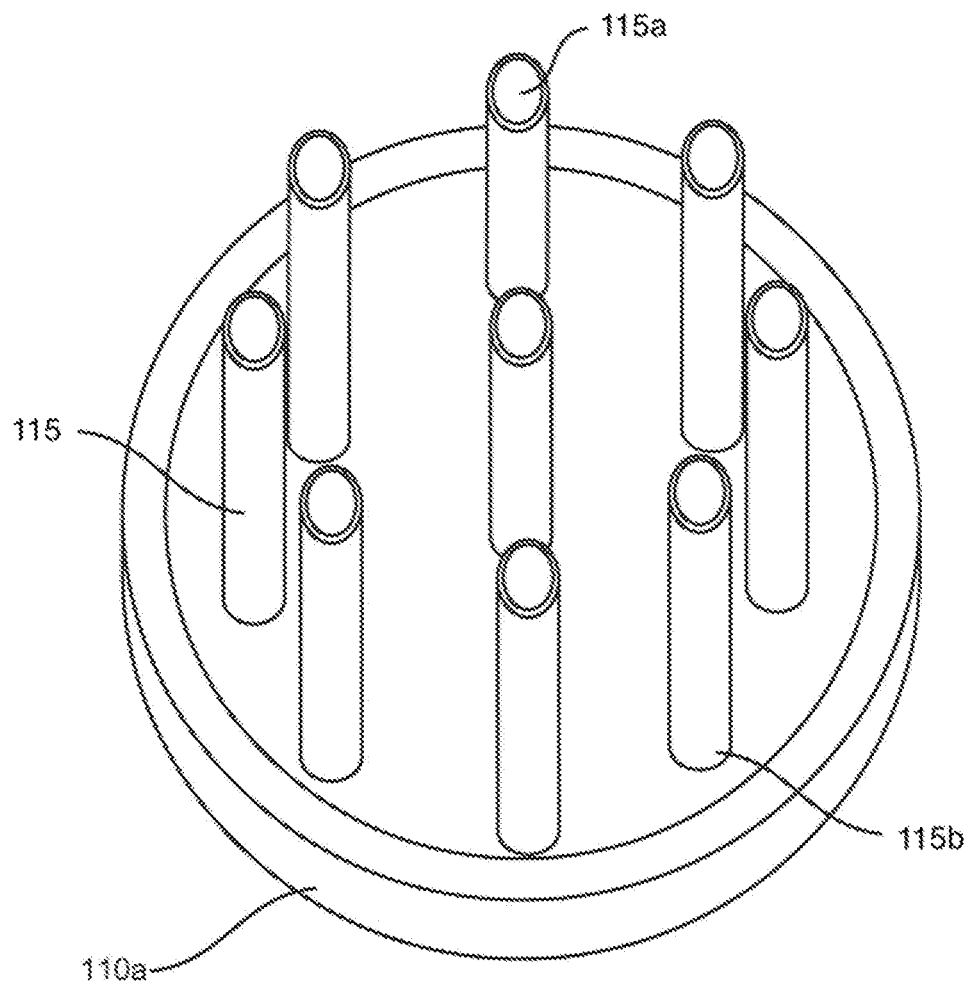
FIG. 2 illustrates a top angled view of an inner portion of a main body base, according to an exemplary embodiment of the present general inventive concept.

FIG. 2 illustrates a top angled view of an inner portion of a main body base 110a, according to an exemplary embodiment of the present general inventive concept.

Figure 3:
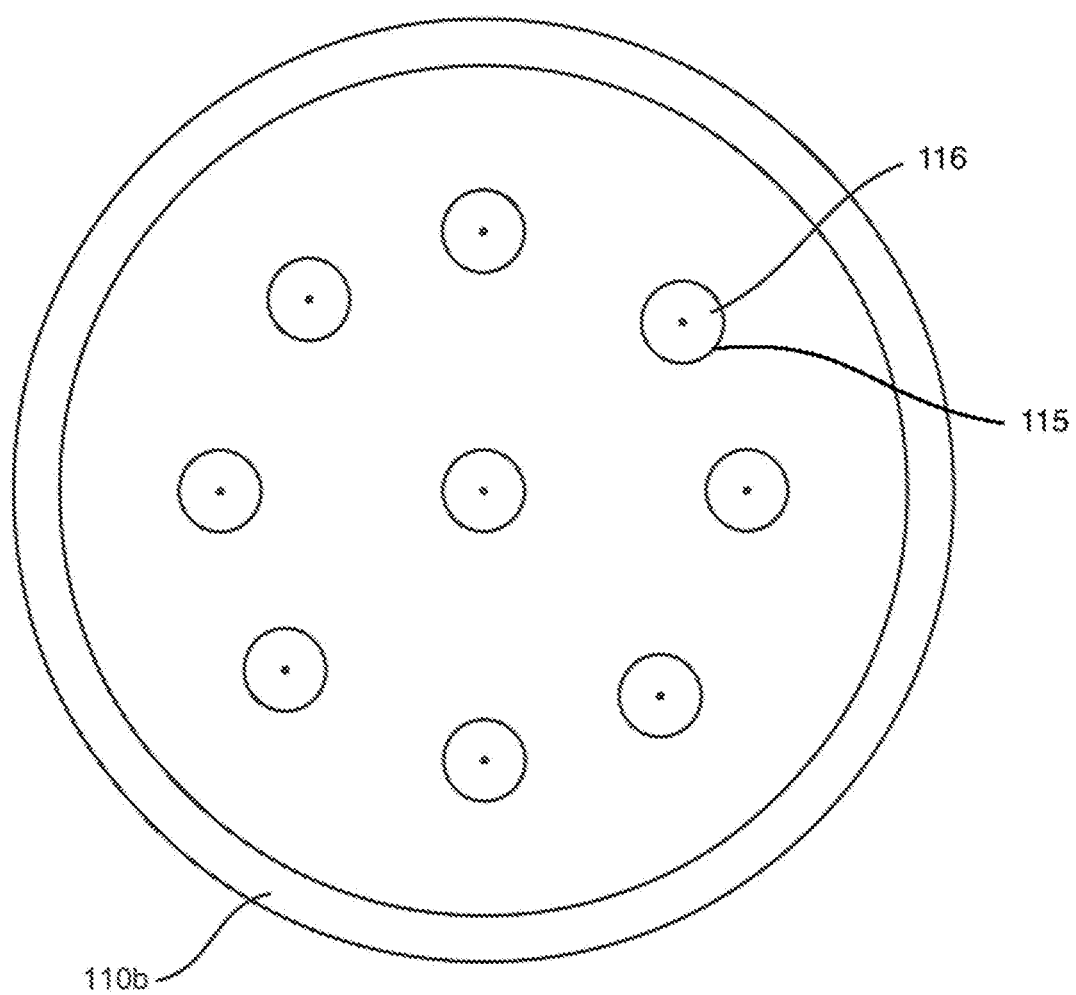
FIG. 3 illustrates a top perspective view of a main body lid, according to an exemplary embodiment of the present general inventive concept.

FIG. 3 illustrates a top perspective view of a main body lid 110b, according to an exemplary embodiment of the present general inventive concept.

Figure 4A:
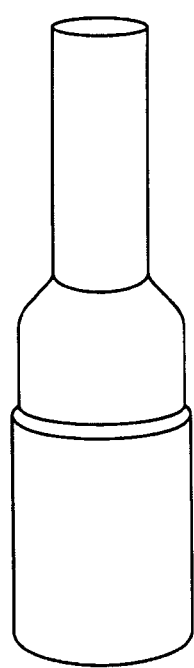
FIG. 4A illustrates a side perspective view of a stem, according to an exemplary embodiment of the present general inventive concept.

FIG. 4A illustrates a side perspective view of a stem 117, according to an exemplary embodiment of the present general inventive concept.

Figure 4B:
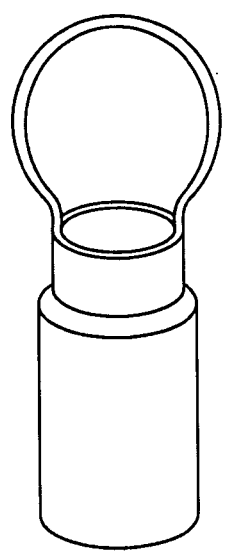
FIG. 4B illustrates a side perspective view of a plug, according to an exemplary embodiment of the present general inventive concept.

FIG. 4B illustrates a side perspective view of a plug 118, according to an exemplary embodiment of the present general inventive concept.

Figure 5:
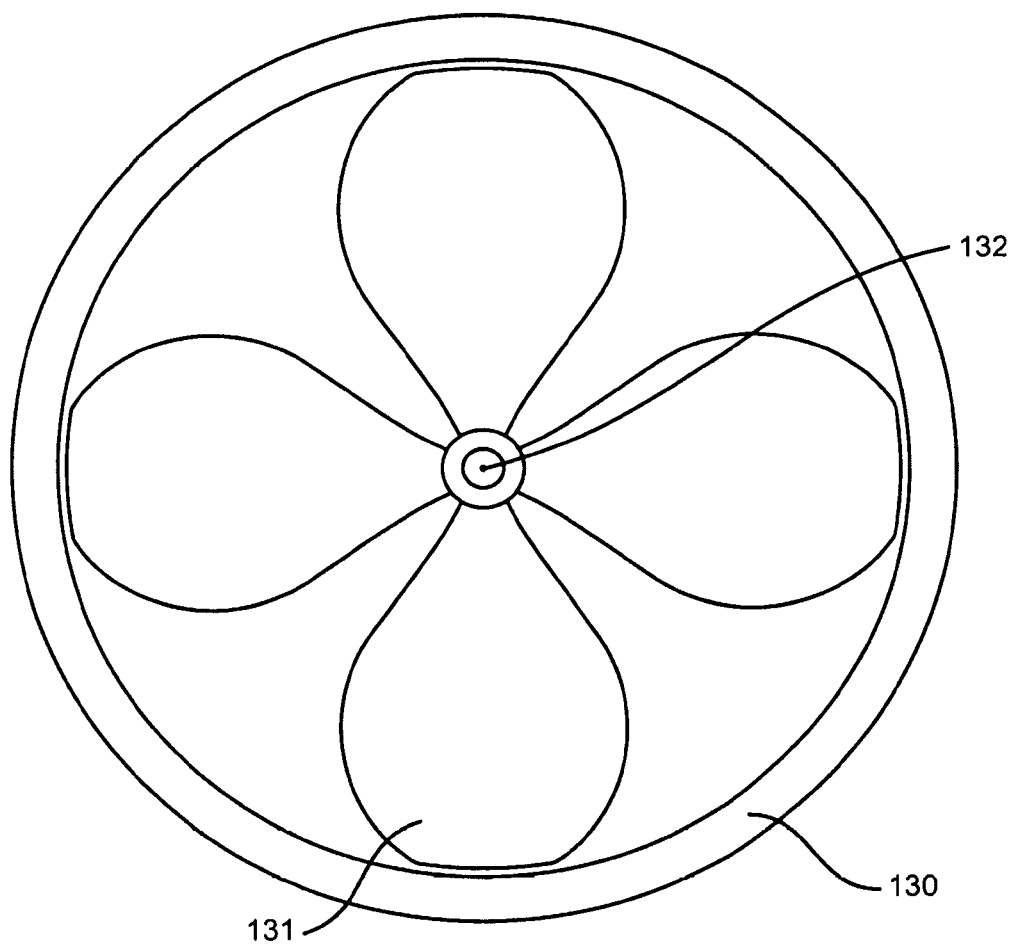
FIG. 5 illustrates a top perspective view of a fan base, according to an exemplary embodiment of the present general inventive concept.

FIG. 5 illustrates a top perspective view of a fan base 130, according to an exemplary embodiment of the present general inventive concept.

Referring to FIGS. 1A and 1B, the herbal dabber vaporizer 100 may include a main body 110, a glass dome 120, and the fan base 130.

The main body 110 may include the main body base 110a, the main body lid 110b, a microprocessor 111, a power button 112, a temperature regulator 113, a display screen 114, a plurality of tubes 115, a plurality of heating elements 116, and a plurality of stems 117.

Referring to FIGS. 1A, 1B, and 5, the fan base 130 may include a plurality of fan blades 131 and a fan motor 132 disposed at a center portion of the plurality of fan blades 131.

The main body base 110a may be disposed below the main body lid 110b, and may include the plurality of tubes 115 disposed therebetween, such that the main body base 110a is connected to the main body lid 110b. The main body base 110a and the main body lid 110b may not be removable from the main body 110. The main body base 110a and the main body lid 110b may have similar sizes and shapes.

The microprocessor 111 may be disposed within the main body 110, may be any type of computer and/or processor known to one of ordinary skill in the art, and may control all of the electrical systems and components within the herbal dabber vaporizer 100, including, but not limited to, the temperature regulator 113, the display screen 114, the plurality of heating elements 116, and the fan motor 132. Alternatively, the electrical systems and components within the herbal dabber vaporizer 100 may be analog, and therefore may not require the microprocessor 111 to function.

The plurality of tubes 115 may be hollow tubes constructed from glass, metal, ceramic, or any other type of material that may withstand high heat intensity.

The plurality of heating elements 116 may include heating coils, ceramic core heating elements, lamps (halogen, incandescent, etc.), flame-controlled heaters, or any other type of heating elements. A clean and efficient option for heating will be a use of inductive heating for each of the plurality of tubes 115. A medical grade stainless steel mass of some type may be installed inside each of the plurality of tubes 115. Induction coils may be installed around the outside of each the plurality of tubes 115. This configuration may create a heater which only has the surgical stainless steel mass exposed to the materials 10.

The plurality of heating elements 116 may be disposed in, around, or about the plurality of tubes 115, and may be activated to emit heat in response to the power button 112 being pressed (i.e., turned on). Also, a heat emitting intensity of the plurality of heating elements 116 may be regulated using the temperature regulator 113, and the display 114 may be any type of digital or analog display disposed on the main body 110 to display a temperature within the herbal dabber vaporizer 100.

The plurality of stems 117 may each be inserted within top apertures 115a disposed at upper ends of the plurality of tubes 115. The plurality of stems 117 may receive materials 10 therewithin. The materials 10 may be herbs, plants, liquids, oils, waxes, or any other type of materials that may be heated, and each of the plurality of stems 117 may include different and/or same materials.

The combination of the plurality of tubes 115 and the plurality of heating elements 116 may also be known as a heating chamber, or a plurality of heating chambers.

The glass dome 120 may include a convex body 121, a convex neck 122, a first opening 123, a second opening 124, and a sealing gasket 125.

The glass dome 120 may be constructed from plastic, glass, metal, ceramic, or any other material known to one of ordinary skill in the art.

The convex body 121 may be disposed at a bottom portion of the glass dome 120, and the concave neck 122 may be disposed at a top portion of the glass dome 120.

The first opening 123 may be disposed at a bottommost portion of the convex body 121, and the second opening 124 may be disposed at a topmost portion of the concave body 122.

The first opening 123 may be larger than the second opening 124, but is not limited thereto.

The convex body 121 may be designed to cover a majority of a top portion of the main body 110 of the herbal dabber vaporizer 100, specifically, the main body lid 110b, such that any vapor generated within the main body 110 enters through the first opening, and funnels through the glass dome 120 such that the vapor may exit out the second opening 124.

The sealing gasket 125 may be disposed along a circumference of the first opening 123, such that an air-tight seal is created when the glass dome 120 is disposed on a top surface of the main body 110, the top surface of the main body 110 otherwise known as the main body lid 110b.

The combination of the glass dome 120 and the plurality of stems 117 may also be known as an extraction chamber, or a plurality of extraction chambers.

When the fan motor 132 is turned on using the power button 112, the fan blades 131 spin, causing a vortex of air to be generated. When the vortex of air is generated by the fan blades 131, the air may move upwards (i.e., in an isolated air flow system and/or isolated air path) into bottom apertures 115b of the plurality of tubes 116, through the plurality of tubes 115 (which include the plurality of heating elements 116 to heat the materials 10 disposed within the stems 117), and may evenly disperse fumes and/or vapor generated by the heated materials 10 within the glass dome 120 to mix the fumes and/or vapor within the glass dome 120 and expel the fumes and/or vapor out from the second opening 124. As a result, a user may smell the fumes and/or vapor mixed and expelled from the second opening 125.

It is important to note that the airpath (i.e., a path of the air generated by the fan blades 131, and which passes through the plurality of tubes 115) is completely isolated from the electronic components of the herbal dabber vaporizer 100, and therefore, the air flowing through the plurality of tubes 115 does not affect, damage, or interfere with the electronic components.

The fan motor 132 may be controlled separately, and may have its speed regulated by a button, knob, and/or or switch, but is not limited thereto.

The stems 117 may also be known as dosing stems 117, as the materials 10 vaporize out of the dosing stems 117 in dosage portions.

Inside each of the stems 117, there may be internal rimless screen installed, and a basket screen which may be easily removed and reinserted. Between these two screens may be an area where the materials 10 may be installed, and from which oils may be extracted during the heating of the plurality of tubes 115.

In a more expensive version of the herbal dabber vaporizer 100, intelligence overheat control by the microprocessor 111 (which may include heat sensors and other components) can be added for very precise temperature control.

In less expensive version of the herbal dabber vaporizer 100, the heat can be controlled by a simple thermostat on the front of the herbal dabber vaporizer 100 and provide rudimentary control over the temperature used for the vaporizing session.

There may also be included dust filters (not illustrated) to be disposed at the bottom of the main body 110, and also on the bottom of the fan base 130.

One further optional component may also be included, specifically a storage container (not illustrated) for the stems 117 and the plugs 118. Inside the storage container would be high temp silicone trays with individual spots that would hold the included stems and plugs keeping them both safe and well organized.

Due to the multiple heating chambers and extraction chambers of the herbal dabber vaporizer 100, different types of herbal materials can be used in each stem 117. This allowing users to combine remedial effects of different herbs into a single medicinal session.

Due to the multiple heating chambers of the herbal dabber vaporizer 100, for which at any time one or more heating chambers can be plugged by the plugs 118 and not used, users have greater control to adjust the strength of their vaporizing sessions.

Due to the multiple heating chambers of the herbal dabber vaporizer 100, users may also opt to load all of the possible dosing stems 117 and use all in a single vaporizing session. This will result in the most possible vaporized essential oil in the least number of draws. This is very important to users treating chronic nausea or chronic pain, as they will receive the most medicinal benefits with the least amount of action for a great benefit.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. An herbal dabber vaporizer to heat materials therein to expel vapor therefrom, the herbal dabber vaporizer comprising:
   a main body, comprising:
      a main body base,
      a main body lid having the same size and shape as the main body base disposed above the main body base,
      at least one tube disposed between the main body base and the main body lid,
      at least one heating element connected to the at least one tube, and
      at least one stem to be inserted at least partially into a top aperture of the at least one tube to receive the materials therein; and
   a glass dome to cover the main body lid and the at least one stem, such that vapor generated from a heating of the materials causes the vapor to be generated within the glass dome, and then expelled out an aperture within the glass dome.

2. The herbal dabber vaporizer of claim 1, wherein the aperture within the glass dome is disposed at a top portion of the glass dome.

3. The herbal dabber vaporizer of claim 1, further comprising:
   a fan base, comprising:
      a plurality of fan blades to spin and generate air that enters a bottom aperture of the at least one tube such that the vapor moves upward out of the at least one stem; and
      a fan motor to cause the fan blades to spin.

4. An herbal dabber vaporizer to heat materials therein to expel vapor therefrom, the herbal dabber vaporizer comprising:
   a main body, comprising:
      a main body base,
      a main body lid disposed above the main body base,
      a plurality of tubes disposed between the main body base and the main body lid,
      a plurality of heating elements disposed around an outside of each of the plurality of tubes,
      a plurality of stems to be inserted at least partially into a top aperture of each of the plurality of tubes to receive the materials therein, and
      a plurality of plugs removably connected to the each of the plurality of tubes to adjust a strength of the vapor expelled; and
   a glass dome to cover the main body lid and the at least one stem, such that vapor generated from a heating of the materials causes the vapor to be generated within the glass dome, and then expelled out an aperture within the glass dome.

* * * * *